United States Patent [19]

Evers et al.

[11] Patent Number: 4,657,708
[45] Date of Patent: Apr. 14, 1987

[54] ETHYNYL-CONTAINING PHTHALOYL HALIDES

[75] Inventors: Robert C. Evers; George J. Moore, both of Dayton, Ohio

[73] Assignee: The United States of America as represented by the Secretary of the Air Force, Washington, D.C.

[21] Appl. No.: 807,155

[22] Filed: Dec. 10, 1985

[51] Int. Cl.$^4$ .................... C07C 63/24; C07C 63/30
[52] U.S. Cl. .................... 260/544 D; 525/421; 528/345
[58] Field of Search .................... 260/544 D, 544 P

[56] References Cited

U.S. PATENT DOCUMENTS 3,609,160  9/1971  Meyer et al. .................... 260/307 D
4,367,329  1/1983  Sankaran et al. .................... 528/183

Primary Examiner—Natalie Trousof
Assistant Examiner—L. Hendriksen
Attorney, Agent, or Firm—Charles E. Bricker; Donald J. Singer

[57] ABSTRACT

Aromatic monomers, each containing at least one o-ethynyl carboxylic acid halide subunit:

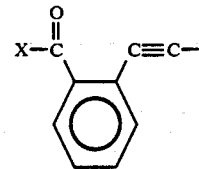

wherein X is Cl or Br. These monomers can be reacted with amines to form aromatic polyamide resins which can be thermally treated to undergo intromolecular cyclization, without evolution of volatiles, into polyimidines.

4 Claims, No Drawings

ETHYNYL-CONTAINING PHTHALOYL HALIDES

RIGHTS OF THE GOVERNMENT

The invention described herein may be manufactured and used by or for the Government of the United States for all governmental purposes without the payment of any royalty.

BACKGROUND OF THE INVENTION

This invention relates to novel monomeric compounds and to a method for their synthesis. In particular, this invention relates to novel ethynyl-substituted aromatic monomers.

Interest in laminates and laminating processes for use in a wide variety of industrial applications has increased considerably in the past few years. Glass fiber laminates, for example, find wide use as structural materials because of their lightweight, high relative strength, and high resistance to corrosion and other damaging effects encountered in an environment subject to extreme fluctuations in temperature and weather. Consequently, a concentrated research effort has evolved in an attempt to develop polymeric materials suitable for use as laminating resins. Such resins must possess a high degree of thermal stability and strength after curing coupled with good solubility characteristics before curing, if they are to be useful for impregnating and bonding the wide variety of laminate materials presently in use.

The research effort referred to above has culminated in the development of several resinous materials that have been found suitable from a stability and strength standpoint. Unfortunately, however, problems have arisen when using such materials due to the evolution of gas during the curing step which occurs after the laminate sheets are impregnated. The curing process which liberates gaseous side products has the deleterious effects of producing voids in the cured laminates which, in turn, substantially weakens the final laminated product.

It is an object of the present invention to provide novel monomers useful in preparing aromatic polyamide resins which can be cured without evolving volatile side products.

Other objects, aspects and advantages of the invention will be readily apparent to those skilled in the art from the following detailed disclosure of the invention.

SUMMARY OF THE INVENTION

In accordance with the present invention there are provided a novel aromatic monomers, each containing at least one o-ethynyl carboxylic acid halide subunit:

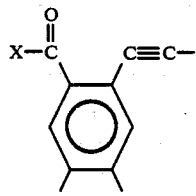
I wherein X is Cl or Br.

The monomers of this invention which contain the above subunit can be reacted with amines to form aromatic polyamide resins which can be thermally treated to undergo intramolecular cyclization, without evolution of volatiles, into polyimidines containing the following subunit:

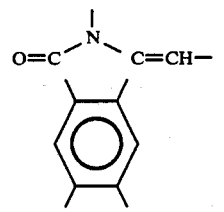
II

The first of the monomers of this invention is tolane-2,4'-dicarbonyl halide of the general formula:

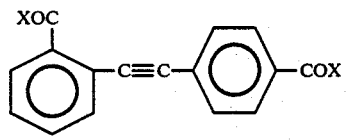

wherein X is Cl or Br.

The second of the monomers of this invention is a 2,5-bis(arylethynyl)terephthaloyl halide of the general formula:

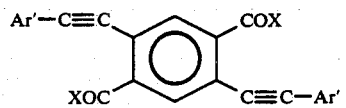

wherein X is Cl or Br and Ar' is a monovalent aromatic radical selected from the group consisting of phenyl and Cl- to C3-substituted phenyl, such as, for example, p-tolyl, p-cumenyl, p-ethylphenyl, and p-propylphenyl.

The third of the monomers of this invention is a 2,4-bis(arylethynyl)isophthaloyl halide of the general formula

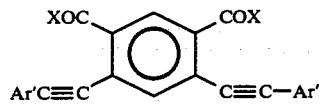

wherein X and Ar' are as described above.

The acid chloride monomers represented above are prepared by treating the corresponding carboxylic acids with thionyl chloride or thionyl bromide. Preparation of the substituted phthalic acids is given in the Examples which follow.

The above acid halide monomers can be condensed with a diamino compound to produce the resins III–V, shown below. More specifically, tolane-2,4'-dicarbonyl halide is condensed with a diamino compound of the general formula $NH_2-Ar-NH_2$ to produce the following resin:

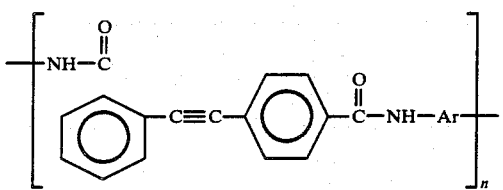

wherein n is an integer and Ar is a divalent aromatic radical having the general formula:

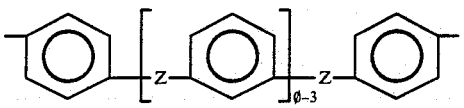

wherein Z is selected from the following: —CH$_2$—, —CO—, —S—, —O—, and —SO$_2$—.

The substituted phthalic acid halide is condensed with a diamino compound, NH$_2$—Ar—NH$_2$, to produce one of the following resins:

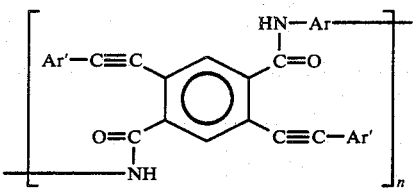

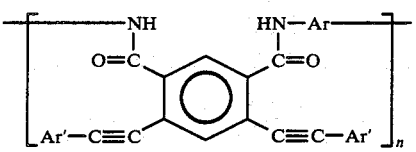

wherein n and Ar are as described above and Ar' is a monovalent aromatic radical selected from the group consisting of phenyl and C1- to C3-substituted phenyl, such as, for example, p-tolyl, p-cumenyl, p-ethylphenyl, and p-propylphenyl.

In the above polycondensations, substantially equimolar amounts of reactants are utilized. The reaction is carried out in the presence of a suitable solvent, one which is inert to the reactants and the resulting polymer, and one in which at least one of the monomers is soluble. Examples of suitable solvents include N-methyl-2-pyrollidone, N,N-dimethylacetamide, N,N-diethylacetamide, N,N-dimethylformamide, tetramethyl urea, sulfolane, and the like.

The polycondensation reaction is carried out at low temperature, i.e. about 0° to 5° C. for about 0.5 to 5 hours. Following the initial reaction period, the reaction mixture may be allowed to warm to room temperature. The mixture is preferably stirred at room temperature for an additional period of about 5 to 72 hours. At the end of the reaction period, the polymer is recovered by a general procedure that is conventionally followed in solution polymerization processes. For example, the reaction mixture is poured into a non-solvent for the polymer, e.g., an alcohol such as methanol, thereby causing the polymer to precipitate from solution. The precipitated polymer is then separated from the liquid by any suitable means, such as by filtration or decantation. The precipitated polymer may be thereafter washed with the so-called non-solvent. If desired, the polymer can be dissolved in a suitable solvent and again precipitated from solution by pouring the solution into a non-solvent. This procedure can be repeated as necessary to further purify the product.

The products of this invention can be heat cured to provide thermoset resins. When heated to temperatures on the order of 150° C., the products of the invention undergo intramolecular cyclization to polyphthalimidines without evolution of volatiles.

When used as a coating material, the products of the invention should be laid down on the substrate and heat cured at temperatures of 175° C. or higher. To prepare laminates, the fabric may be impregnated with a solvent solution of the polymer, e.g., methane sulfonic acid, then rinsed with a non-solvent for the polymer, e.g., methanol, to precipitate the polymer in the interstices of the fabric and to remove the solvent. The fabric is then dried to remove the non-solvent. The dried fabric can then be laid up and heated to cross-link the resin solids. Modest pressures on the order of 15-200 psig are sufficient, if employed. Curing temperatures on the order of 150°-250° C., preferably about 170°-220° C. are employed for curing times on the order of about 1 to 12 hours. The laminates may be post cured for 10 to 50 hours at temperatures of about 200°-300° C. Alternatively, the laminate fabric may be dusted with dry resin powder, instead of the solvent procedure described above.

The following examples illustrate the invention:

EXAMPLE I

Tolane-2,4'-dicarbonyl Chloride 2,4'-Tolanedicarboxylic acid (2.40 g, 0.009 moles) was stirred at room temperature for 48 hours in 35 ml of thionyl chloride (redistilled from boiled linseed oil). This suspension was then refluxed for eight hours to give a clear, light red solution. The excess thionyl chloride was then stripped off to give a grey solid, mp 79°-85° C. Recrystallization from hexane afforded 1.38 g (51% yield) of tolane-2,4'-dicarbonylchloride as a waxy, off-white solid which after drying at 58° C./0.10 mm Hg exhibited mp 184.5°-185.5° C.

Anal. Calc'd for C$_{16}$H$_8$Cl$_2$O$_2$: C, 63.39; H, 2.66; Cl, 23.39; MW, 266. Found: C, 63.42; H, 2.12; Cl, 23.21; MW, 266 (mass spectrum).

EXAMPLE II 4,6-Bis(phenylethynyl)isophthaloyl Chloride

Bromine (395.5 g, 2.472 mole) (dried over concentrated sulfuric acid) was added dropwise to stirred 4,6-dibromo-1,3-xylene (150 g, 0.568 mole) in an ultraviolet irradiation apparatus. Approximately 90 ml of bromine was added over 2.5 hour with the temperature being maintained at 120°-130° C. An additional 20 ml was added over two hours at 130°-150° C. and the final 17 ml was added over two hours at 150°-160° C. After the bromine was completely taken up, the yellow reaction mixture was distilled in portions to give a 1,3-bis(dibromomethyl)-4,6-dibromobenzene as a white solid bp 178°-182° C./0.02 mm Hg. Recrystallization from absolute ethanol yielded a total of 259 g (79% yield) of white crystals, mp 115°-118° C.

Anal. Calc'd for C$_8$H$_4$Br$_6$: C, 16.58; H, 0.69; MW, 580. Found: C, 16.49; H, 0.67; MW, 580 (mass spectrum).

An aqueous solution of silver nitrate (71.0 g, 0.418 mole) in 544 ml of water added dropwise over three hours to a stirred solution of 1,3-bis(dibromomethyl)-4,6-dibromobenzene (40.0 g, 0.069 mole) in 300 ml cellosolve at 80°–85° C. The green reaction mixture was stirred at temperature for an additional 3.5 hours and filtered while hot. The collected precipitate was washed thoroughly with water and suction dried on the frit. Water added to the filtrate produced a white product that was recrystallized from cyclohexane to yield 6.1 g of white crystals. The dried green precipitate was extracted with hot benzene and the resulting material recrystallized from cyclohexane to yield 7.1 g of white crystals. Combined yield of 4,6-dibromoisophthalaldehyde was 13.6 g (66% yield), mp 188°–191° C.

Anal. Calc'd for $C_8H_4Br_2O_2$: C, 32.91; H, 1.38; MW, 292. Found: C, 32,83; H, 1.46; MW, 292 (Mass spectrum).

The 4,6-dibromoisophthaladehyde (16.4 g, 0.056 mole) was dissolved in a solution of triethylamine (280 ml) and pyridine (315 ml) under a nitrogen atmosphere. To the stirred solution palladium acetate (0.28 g, 0.0013 mole) and triphenyl phosphine (0.70 g, 0.0027 mole) were added. Phenylacetylene (14.3 g, 0.140 mole) was added dropwise over the course of an hour to the red reaction mixture at 45°–50° C. The reaction was continued an additional 3.5 hours. It was then cooled and poured into a sulfuric acid-ice mixture. The resultant yellow precipitate was collected by filtration, thoroughly washed with water, and suction dried on the frit. Recrystallization of the material from heptane yielded 12.0 g (64% yiled) of 4,6-bis(phenylethynyl)-isophthalaldehyde, mp 170°–172° C.

Anal. Calc'd for $C_{24}H_{14}O_2$: C, 86.21; H, 4.22; MW, 334. Found: C, 85.56; H, 4.40; MW, 334 (Mass spectrum).

4,6-Bis(phenylethynyl)isophthalaldehyde (7.8 g, 0.023 mole) was dissolved in acetone (distilled from solid potassium permanganate) and the solution was chilled to 0° C. A chromium trioxide-sulfuric acid solution was prepared by slurrying 26.7 g of chromium trioxide in 23 ml of concentrated sulfuric acid and 40 ml of distilled water. This solution was diluted in the cold with distilled water to 110 ml. A portion of this solution (16.9 ml) was added dropwise over 1.5 hours to the stirred yellow acetone solution. During this period the color of the reaction mixture changed from yellow to brown and finally to green. After an additional 20 hours of reaction, the mixture was warmed to room temperature and poured into a vessel containing ice and water. The yellow precipitate was collected by filtration and washed thoroughly with water. Suction drying on the frit yielded 7.3 g (85.5% yield) of the light yellow 4,6-bis(phenylethynyl)isophthalic acid.

Anal. Calc'd for $C_{24}H_{14}O_4$: C, 78.68; H, 3.85; MW, 366. Found: C, 78.08; H, 3.95; MW, 366 (mass spectrum).

4,6-Bis(phenylethynyl)isophthalic acid (4.0 g, 0.0109 mole) was slurried in 170 ml of thionyl chloride (freshly distilled from boiled linseed oil) for 30 minutes. To the reaction mixture, a few drops of N,N-dimethylformamide was added to effect solution. The reaction mixture was stirred between 35°–40° C. for 16 hours. Removal of the excess thionyl chloride under reduced pressure yielded an orange-yellow solid. Recrystallization from hexane gave 16 g (36.4% yield) of 4,6-bis(phenylethynyl)isophthaloyl chloride as light yellow crystals, mp 157°–160° C.

Anal. Calc'd for $C_{24}H_{12}Cl_2O_2$: C, 71.48; H, 3.00; MW, 402. Found: C, 70.95; H, 3,32; MW, 402 (mass spectrum).

EXAMPLE III 2,5-Bis(phenylethynyl)terephthaloyl Chloride (Method 1)

2,5-Dibromo-1,4-xylene (43.0 g, 0.163 mole) was dissolved in 550 ml of glacial acetic acid and 550 ml of acetic anhydride. To the vigorously stirred solution at 0°–5° C. was cautiously added 90 ml of concentrated sulfuric acid. With the temperature being maintained at −5° C., chromium trioxide (93.0 g, 0.930 mole) was gradually added over a period of 1.5 hours, care being taken to keep the reaction temperature below 5° C. The red reaction mixture gradually became very viscous and took on a deep green coloration. After being stirred for four more hours, it was then brought to room temperature and poured with stirring into five liters of cold water. The white precipitate was isolated by filtration and washed on the frit with water until no green color appeared in the washings. The white solid was stirred in two liters of 2% sodium carbonate solution for one hour, isolated by filtration, and washed well on the frit with water. Air drying overnight afforded 45.5 g (56% yield) of unpurified 2,5-dibromo-α,α,α',α'-tetraacetoxy-1,4-xylene, mp 200°–210° C. Recrystallization of an analytical sample from isopropanol gave mp 219°–221° C.

Anal. Calc'd for $C_{16}H_{16}O_8Br_2$: C, 38.73; H, 3.25; Br, 32.22. Found: C, 39.01; H, 3.08; Br, 32.11.

Unpurified 2,5-dibromo-α,α,α',α'-tetraacetoxy-1,4-xylene (60.5 g, 0.122 mole) was dissolved with stirring in three liters of hot ethanol. Then 450 ml of water was added followed by 75 ml of concentrated sulfuric acid which was added very slowly. After being allowed to reflux for an hour, the reaction mixture was diluted with 900 ml of hot water. Cooling overnight at −10° C. resulted in the recrystallization of 30.9 g (87% yield) of 2,5-dibromoterephthalaldehyde, mp 184°–189° C. (lit 189°–190.5° C.) which was isolated by filtration.

Anal. Calc'd for $C_8H_4O_2Br_2$: C, 32.91; H, 1.38; Br, 54.75; MW, 292. Found: C, 32.68; H, 0.90; Br, 54.60; MW, 292 (mass spectrum).

A solution of diphenyl(α-chlorobenzyl)phosphonate (28.70 g, 0.080 mole) in 150 ml of dry dimethylsulfoxide was cooled to 0°–5° C. Sodium hydride (3.84 g, 0.160 mole) (as a 50% suspension in mineral oil) was added to the rapidly stirred solution. With the temperature being maintained at 0°–5° C., 2,5-dibromoterephthalaldehyde (11.64 g, 0.04 mole) slurried in 50 ml of dry dimethylsulfoxide was added over a five minute period. Considerable foaming took place during the addition. After being allowed to continue at room temperature overnight, the reaction mixture was added to 250 ml of ice water. The resultant beige precipitant was isolated by filtration and washed on the frit with water. Drying at 60° C./1.0 min Hg for two hours yielded 16.63 g of beige product, mp 130°–235° C. The crude product was extracted with 400 ml of heptane for two hours in an extraction apparatus. The heptane solution upon cooling gave 8.45 g (48% yield) of 1,4-bis(phenylethynyl)-2,5-dibromobenzene as light yellow crystals, mp 155°–158° C. An additional 3.5 g of slightly lower melting material was recovered from the mother liquor.

Anal. Calc'd for $C_{22}H_{14}Br_2$: C, 60.58; H, 2.77; Br, 36.65; MW, 436. Found: C, 60.85; H, 2.52; Br, 36.41; MW, 436 (mass spectrum).

n-Butyl lithium (2.11 g, 0.033 mole) (14.25 ml of a 2.32M solution in hexane) was added over five minutes to a vigorously stirred solution of 1,4-bis(phenylethynyl)2,5-dibromobenzene (6.54 g, 0.015 mole) in 500 ml of ether at 0° C. The initial yellow slurry took on a brown color for several minutes before a dull yellow precipitate was formed. After being allowed to stir for three hours at 0° C. under a nitrogen blanket, the reaction mixture was added to a slurry of dry ice in 300 ml of ether. This slurry was stirred for five hours and the excess dry ice was then allowed to evaporate. The ether solution was then extracted with 500 ml of a very dilute aqueous potassium hydroxide solution which was in turn extracted with 50 ml of ether. The cooled aqueous layer was acidified with dilute sulfuric acid to give a yellow precipitate which was isolated by filtration. Drying for three hours at 60° C./1.0 mm Hg yielded 5.10 g of crude product, mp>360° C. with prior shriveling at 190°–200° C. Recrystallization from isopropanol afforded 2.90 g (53% yield) of 2,5-bis(phenylethynyl)-terephthalic acid as a powdery yellow solid, mp>360° C. with shrinking at 270°–275° C.

Anal. Calc'd for $C_{24}H_{14}O_4$: C, 78.68; H, 3.85; MW, 366. Found: C, 78.72; H, 3.65; MW, 366 (mass spectrum).

A mixture of 2,5-bis(phenylethynyl)terephthalic acid (2.20 g, 0.006 mole) suspended in 40 ml of thionyl chloride (redistilled from boiled linseed oil) was stirred at reflux overnight to give a deep yellow solution. The excess thionyl chloride was stripped off to give a deep yellow solid which was recrystallized from 150 ml of heptane. 2,5-Bis(phenylethylyl)terephthaloyl chloride (1.35 g, 56% yield) was obtained as deep yellow crystals. mp 179°–181° C. with prior shrinking at 176° C.

Anal. Calc'd for $C_{24}H_{12}O_2Cl_2$: C, 71.48; H, 3.00; MW, 403. Found: C, 71.30; H, 2.91; MW, 403 (mass spectrum).

EXAMPLE IV 2,5-Bis(phenylethynyl)terephthaloyl Chloride (Method 2)

2,5-Dibromoterephthalaldehyde (29.2 g, 0.100 mole) and phenylacetylene (25.5 g, 0.250 mole) were dissolved at 80° C. under nitrogen in a mixture of freshly distilled triethylamine (200 ml) and pyridine (200 ml). Palladium acetate (0.54 g, 0.0024 mole) and triphenylphosphine (1.26 g, 0.0048 mole) were added to the vigorously stirred red solution. The resultant exotherm did not subside for fifteen minutes and a voluminous white precipitate was formed. After an additional hour at reflux, the red slurry was added with vigorous stirring to a sulfuric acid ice mixture. The slightly gummy brown precipitate was washed several times with water in a blender and isolated by filtration. It was dried overnight over phosphorus pentoxide at 80° C./1.0 mm Hg to yield 39.5 g of light brown solid, mp 145°–162° C. The crude product was recrystallized from toluene to give 17.5 g of golden crystals, mp 174°–179° C. Subsequent recrystallization from ethyl acetate gave 14.6 g (44% yield) of 2,5-bis(phenylethynyl)terephthalaldehyde, mp 179°–181° C.

Anal. Calc'd for $C_{24}H_{14}O_2$: C, 86.21; H, 4.22; MW, 334. Found: C, 86.42; H, 4.42; MW 334 (mass spectrum).

2,5-Bis(phenylethynyl)terephthalaldehyde (5.01 g, 0.015 mole) was stirred under nitrogen in 300 ml of redistilled acetone at 0° C. Then a chromium trioxide/sulfuric acid solution (11.25 ml containing 3.0 g, 0.030 mole of chromium trioxide) was pipetted into the yellow slurry which was then stirred for four hours at 0° C. An additional 1.88 ml of chromium trioxide/sulfuric acid solution was then added and the reaction was allowed to proceed at 0° C. for an additional two hours. The resultant slurry was poured into 600 ml of ice water and the yellow precipitate was isolated by filtration. After being washed well on the frit with water, the yellow solid was allowed to dry on the frit. Drying for one hour at 50° C./1.0 mm Hg over phosphorus pentoxide afforded 5.40 g (98% yield) of 2,5-bis(phenylethynyl)terephthalic acid, mp>360° C. with slight shrinking at 260°–270° C.

2,5-Bis(phenylethynyl)terephthalic acid (5.40 g, 0.015 mole) was stirred at room temperature in 320 ml of thionyl chloride (distilled from boiled linseed oil). Several drops of N,N-dimethylformamide were added to the yellow slurry which was stirred overnight at room temperature. The small amount of insolubles which remained then went into solution after ten minutes at reflux. The excess thionyl chloride was stripped off at reflux to given an orange solid which was recrystallized from heptane to give 2.4 g (40% yield) of 2,5-bis(phenylethynyl)terephthaloyl chloride, mp 174°–180° C.

EXAMPLE V

Polycondensation of Tolane-2,4'-dicarbonyl Chloride with 4,4'-(m-phenylenedioxy)dianiline)

4,4'-(m-Phenylenedioxy)dianiline (0.6724 g, 0.0023 mole) was dissolved in 5 ml of N-methyl-2-pyrollidone (distilled from calcium hydride) and the resultant water-white solution was cooled to 0° C. Tolane-2,4'-dicarbonyl chloride (0.6972 g, 0.0023 mole) followed by eight ml of N-methyl-2-pyrollidone was added to the vigorously stirred solution. The resultant pale green solution was stirred at 0° C. for an hour and at room temperature for 36 hours. The polymer was precipitated from methanol and was washed several times with methanol in a continuous extraction apparatus for 36 hours. Drying at 58° C./0.10 mm Hg for 16 hours gave 1.0 g (83% yield) of cream colored polymer: $\eta_{inh}=0.31$ dl/g (N,N-dimethylacetamide, 25° C., 0.2 g/dl).

Anal. Calc'd for $(C_{34}H_{22}N_2O_4)_n$: C, 78.15; H, 4.24; N, 5.36. Found: C, 76.87, H, 4.23; N, 5.40.

EXAMPLE VI

Polycondensation of 2,5-Bis(phenylethynyl)terephthaloyl Chloride with 4,4'-(m-phenylenedioxy)dianiline)

4,4'-(m-phenylenedioxy)dianiline (0.5847 g, 0.0020 mole) was dissolved in 10 ml of N,N-dimethylacetamide (distilled from calcium hydride). The resultant water white solution was cooled under nitrogen to 0° C. 2,5-Bis(phenylethynyl)terephthaloyl chloride (0.8065 g, 0.0020 mole) was added as a solid to the vigorously stirred solution over a five minute period. Three ml of N,N-dimethylacetamide were used to wash residual diacid chloride into the reaction flask. The resultant yellow slurry gradually became a clear pale green solution over the course of thirty minutes. After being stirred for three hours at 0° C. and sixteen hours at room temperature, the slightly viscous solution was a pale yellow color. The polymer was isolated by precipitation from methanol and washed several times with methanol in a blender. Drying at 58° C./0.10 mm Hg for eight hours and at 100° C./0.10 mm Hg for four hours gave a re-scan after the original scan was taken to 450° C. in air.

TABLE

| Polymer No. | Monomer Acid Chloride | Monomer Diamine | Inh. Visc. (a) dl/g | Tg-init (°C.) | Tcycl Onset (°C.) | Tcycl Peak (°C.) | Tg-final (°C.) |
|---|---|---|---|---|---|---|---|
| I | Tolane-2,4'dicarbonyl chloride | 4,4'Oxydianiline | 0.29 | (b) | 170 | 252 | 270 |
| II | Tolane-2-4'-dicarbonyl dicarbonyl chloride | 4,4-'(m-phenylene-dioxy)dianiline | 0.31 | 182 | 190 | 242 | 220 |
| III | 2,5-bis(phenylethynyl) terephthaloyl chloride | 4,4'-Oxydianiline | 0.30 | (b) | 200 | 295 | (c) |
| IV | 2,5-bis(phenylethynyl) terephthaloyl chloride | 4,4'-(m-phenylene-dioxy)dianiline | 0.51 | 189 | 222 | 250 | (c) |
| V | 4,6-bis(phenylethynyl) isophthaloyl chloride | 4,4'-Oxydianiline | 0.20 | (b) | 185 | 250 295 | (c) |
| VI | 4,6-bis(phenylethynyl) isophthaloyl chloride | 4,4'-(m-phenylene-dioxy)dianiline | 0.26 | 174 | 195 | 255 280 | (c) |

Notes:
(a) Methane sulfonic acid, 0.2 g/dl, 25° C.
(b) Tg-init obscured by Tcycl.
(c) No Tg-final observed after scanning to 450° C.

gave 1.20 g (96% yield) of fluffy yellow polymer: $\eta_{inh} = 0.51$ dl/g (MeSO$_3$H, 25° C., 0.2 g/dl).

Anal. Calc'd for $(C_{42}H_{38}N_2O_4)_n$: C, 81.01; H, 4.21; N, 4.50. Found: C, 81.07; H, 4.24; N, 4.38.

EXAMPLE VII

Polycondensation of 2,5-Bis(phenylethynyl)terephthaloyl Chloride with 4,4'-Oxydianiline 4,4'-Oxydianiline (0.2880 g, 0.0014 mole) was dissolved in 5 ml of N-methyl-2-pyrollidone (distilled from calcium hydride) and the resultant water-white solution was cooled under nitrogen to 0°–5° C. 2,5-Bis(phenylethynyl)terephthaloyl chloride (0.5800 g, 0.0014 mole) was added to the vigorously stirred solution with four ml of solvent being used to wash residual monomer into the reaction flask. The reaction temperature was maintained at 0°–5° C. for several hours and at room temperature for several days. The resultant clear yellow solution was added to 100 ml of methanol and the precipitated polymer was isolated by filtration. It was washed with methanol in a blender and extracted for several days with hot methanol in an extraction apparatus. Drying at 100° C./0.10 mm Hg for six hours yielded 0.68 g (92% yield) of pale yellow polymer: $\eta_{inh} = 0.67$ dl/g (MeSO$_3$H, 25° C., 0.2 g/dl).

Anal. Calc'd for $(C_{36}H_{34}N_2O_3)_n$: C, 81.34; H, 4.17; N, 5.27. Found: C, 81.27; H, 4.14; N, 5.09.

EXAMPLE VIII

The glass transition temperatures of several polyamides prepared generally by the procedures given in Examples V–VII, using the monomers given in the Table, are set forth in the following Table. The glass transition temperature (second order transition temperature) was measured using a Differential Scanning Calorimeter (DuPont 990 Thermal Analyzer) and range 25°–450° C. with a scan speed of 10° C./min. In all cases there is a strong exotherm (T cycl) indicative of the intramolecular cyclization reaction of the polyamide to polyphthalimidine structure. Tg-final was recorded on

EXAMPLE IX

The polymer listed as polymer no. IV in the preceding table was heated in an oven under nitrogen at 255° C. for 16 hours. The resulting polyphthalmidine had a Tg-init of 278° C. Differential scanning calorimetry and thermomechanical analysis revealed an exotherm at 367° C., indicating incomplete cyclization. Additionally, the IR spectrum exhibited bands indicative of the uncyclized polyamide structure as well as the polyphthalimidine structure.

Various modifications may be made in the present invention without departing from the spirit of the invention or the scope of the appended claims.

We claim:

1. A 2,5-bis(arylethynyl)terephthaloyl halide of the general formula

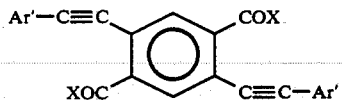

wherein X is Cl or Br and Ar' is a monovalent aromatic radical selected from the group consisting of phenyl and C$_1$ to C$_3$-substituted phenyl.

2. The compound of claim 1 wherein X is —Cl and Ar' is phenyl.

3. A 2,4'-bis(arylethynyl)isophthaloyl halide of the general formula

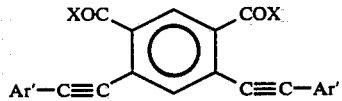

wherein X is Cl or Br and Ar' is a monovalent aromatic radical selected from the group consisting of phenyl and C$_1$ to C$_3$-substituted phenyl.

4. The compound of claim 3 wherein X is —Cl and Ar' is phenyl.

* * * * *